(12) United States Patent
Schmidt et al.

(10) Patent No.: US 7,558,427 B2
(45) Date of Patent: Jul. 7, 2009

(54) METHOD FOR ANALYZING IMAGE DATA

(75) Inventors: Volker Schmidt, Erlangen (DE); Hans Schüll, Weisendorf (DE); Werner Striebel, Schwarzenbruck (DE)

(73) Assignee: Siemens Aktiengesellschaft, Munich (DE)

( * ) Notice: Subject to any disclaimer, the term of this patent is extended or adjusted under 35 U.S.C. 154(b) by 715 days.

(21) Appl. No.: 11/185,325

(22) Filed: Jul. 20, 2005

(65) Prior Publication Data

US 2006/0017986 A1    Jan. 26, 2006

(30) Foreign Application Priority Data

Jul. 22, 2004    (DE)    .................. 10 2004 035 669

(51) Int. Cl.
    *G06K 9/62*    (2006.01)
(52) U.S. Cl. .................. 382/228; 382/232; 382/254
(58) Field of Classification Search .................. 382/228,
    382/284, 312, 234, 304, 232, 276, 302, 254;
    358/471, 468, 1.15, 1.13, 448; 430/213,
    430/487, 215; 396/429; 348/761, 218.1;
    428/32.51, 914, 500, 480; 359/252, 250
    See application file for complete search history.

(56) References Cited

U.S. PATENT DOCUMENTS 6,947,039 B2 *  9/2005  Gerritsen et al. ............ 345/419
7,194,119 B2 *  3/2007  Zahlmann et al. ........... 382/128

FOREIGN PATENT DOCUMENTS

EP    0 768 624 A2    4/1997
EP    0 947 961 A2    10/1999

* cited by examiner

*Primary Examiner*—Sheela C Chawan

(57) ABSTRACT

The invention relates to a method for analyzing image processing procedures, in which unprocessed original image data is stored, stored original image data is retrieved, retrieved original image data is processed, the individual processing steps during the processing of the image data are in some instances stored together with the respective processing step parameter values, and the processed image data is stored such that it can be assigned to the processing steps stored during its processing and in some instances processing step parameter values. According to the invention the processed image data is analyzed statistically and the result of the statistical analysis is stored such that it can be assigned to the stored processing steps and in some instances processing step parameter values. The original image data is optionally included in the statistical analysis of the processed image data.

19 Claims, 2 Drawing Sheets

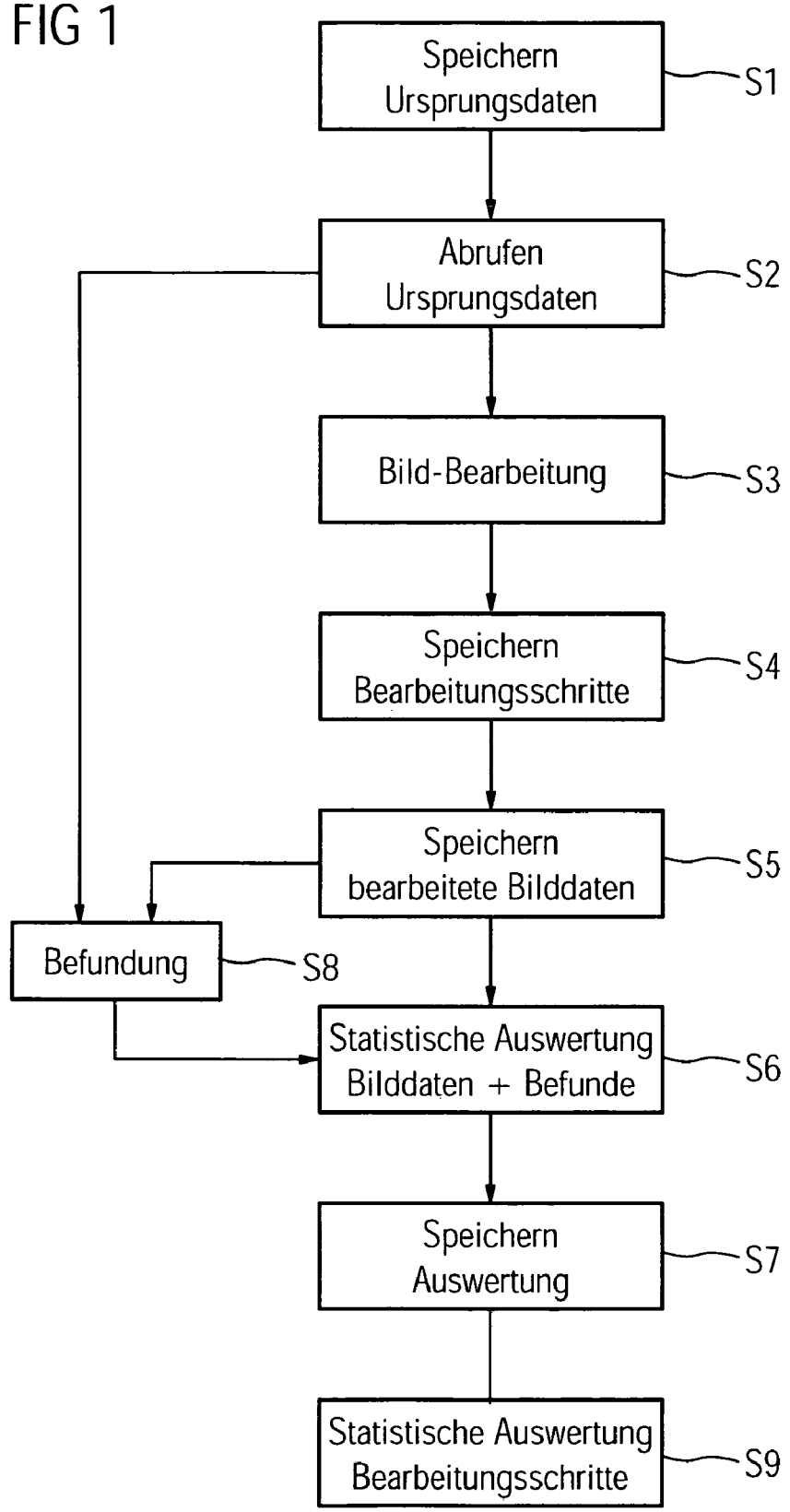

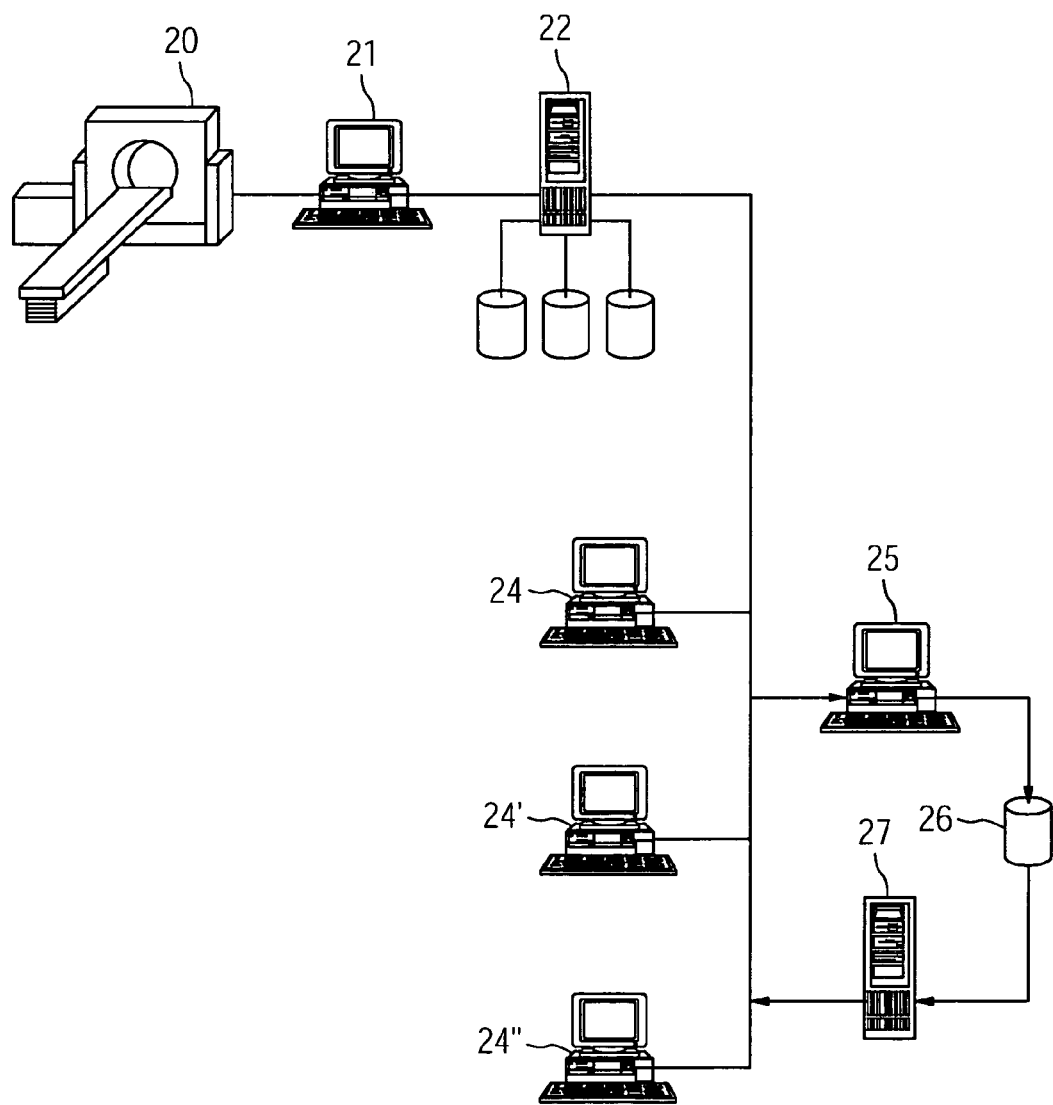

METHOD FOR ANALYZING IMAGE DATA

CROSS REFERENCE TO RELATED APPLICATIONS

This application claims priority to the German application No. 10 2004 035 669.6, filed Jul. 22, 2004 which is incorporated by reference herein in its entirety.

FIELD OF INVENTION

The invention relates to a method for the statistical analysis of image processing procedures.

BACKGROUND OF INVENTION

Digital image data is widely used both privately and professionally. Digital image data can originate from digital photographs as well as from the digitization of non-analog images or examinations using X-ray equipment, magnetic resonance equipment (MR), computed tomography equipment (CT), ultrasound equipment, microscopes, fundus cameras, endoscopes and video recordings, etc. In a technical environment digital image data is used for example for scientific material testing of items, for baggage checks using X-ray equipment in security controls, in biometric methods for personal identification, etc. In a medical environment it is generated by diagnostic imaging devices carrying out examinations of the human body or for example in the laboratory using microscopes, for example to examine tissue samples in the pathology laboratory.

SUMMARY OF INVENTION

Depending on its source or means of generation, the information content of image data is extremely extensive, thus requiring a large memory and long processing times, if for example medical personnel have to look at all the images from a CT examination. A wide variety of processing procedures can be used for optical highlighting of the information required for the respective purpose, with the possibility if required of deleting excessive or redundant information content in order to reduce the memory requirement. For example various compression methods are used to maintain the optical impression of a digital image as can be registered by the human eye whilst at the same time deleting information that cannot be or is not readily registered. When image data is used to analyze specific characteristics of the imaged body or object, certain image features must also frequently be highlighted and rendered such that they can be registered more easily by the human eye, by for example enlarging image regions of particular interest (roi=regions of interest), enhancing contrast, suppressing background noise (electronic cleansing) or highlighting any imaged contours more strongly.

In medical diagnostics image data is generated by so-called modalities, such as X-ray equipment, MR or CT, fundus cameras or endoscopes and used to evaluate findings. Findings are evaluated at digital workstations, both in local and in distributed work environments. Technical advances in the modalities have made the information content of the medical image data increasingly extensive and complex, e.g. 3D or 4D data is increasingly used in addition to 2D data. The large data sets of a CT 3D layer examination for example mean that a great deal of time is required to examine the individual sections. The requirements for data processing technology, e.g. transmission, storage and image processing, become more stringent as a result as do the requirements relating to the quality of the findings evaluation or the medical personnel evaluating the findings.

From a technical point of view algorithms are available, which take into account these more stringent requirements, in that image data can be compressed or manipulated or converted to a different display format, as is the case for example in virtual endoscopy. Known compression algorithms can thereby operate both with and without loss in respect of the information content of the image data. Algorithms for manipulating image data can operate similarly with or without loss, by for example processing color scales, gray values or the scope of the image. Algorithms for image manipulation for example allow the highlighting of image features, computer-aided diagnosis (CAD), digital subtraction angiography, automatic contour highlighting (segmentation), etc.

However it is frequently not known beforehand, which manipulations can be carried out on the image data, without the quality of the result being adversely affected or information being lost relating to the respective purpose. For example it is not clear to what extent medical images can be compressed with a level of loss, without adversely affecting the information they provide in respect of the relevant medical diagnosis. It is similarly unclear which compression algorithms are more appropriate and which less so. Quality control in medicine therefore provides for at least one primary finding to be evaluated solely on the basis of uncompressed images. This ensures that the full information content of the original image data, obtained for example from one modality, can be taken into account. However this means that the maximum memory requirement of the original image data imposes its full load on system resources. Also image manipulation, which might possibly simplify findings evaluation, cannot be used.

An object of the invention is therefore to analyze image processing procedures for manipulating image data automatically in respect of result quality. The invention can be applied in all environments, in which image data is used, both in a technical environment and in medicine. The object of the invention in medicine is in particular to analyze image processing procedures automatically during findings evaluation or analysis of the image data in respect of the quality of the findings evaluation or diagnosis during everyday medical or radiological routine operation.

This object is achieved by the claims.

The invention therefore provides a method for analyzing image processing procedures, in which unprocessed original image data is stored, stored original image data is retrieved, retrieved original image data is processed, the individual processing steps during the processing of image data are stored in some instances together with respective processing step parameter values, the processed image data is stored such that it can be assigned to the processing steps and in some instances processing step parameter values stored during its processing, with the processed image data being analyzed statistically and the result of the statistical analysis being stored such that it can be assigned to the stored processing steps and in some instances processing step parameter values. The invention thereby allows statistical quality tools to be used to analyze everyday routine operation during image processing automatically, without routine operation being adversely affected as a result, and therefore to verify the question whether image manipulation algorithms or compression methods modify the result during ongoing operation. In other words: a person, e.g. a member of the medical personnel, can carry out image processing as usual, while the statistical analysis runs in the background so to speak without adversely affecting routine operation. The algorithms applied during image processing can be evaluated automatically in a wide range of test scenarios.

Findings are advantageously evaluated or processed image data is advantageously analyzed, with the results being included in the statistical analysis. This means that in particular in work environments in which image processing is carried out in respect of a finding to be retained in the result or an analysis or diagnosis, the quality of this result can be included in statistical quality control and can be used to analyze the respective image processing procedure. In other words the quality of the findings evaluation can be monitored. The analysis also advantageously takes place as a function of a feature of the processed image data, e.g. its memory requirement. This provides an objectively determinable feature for analysis, which can for example allow conclusions to be drawn about the system resource requirement of the processed image data.

The statistical analysis can also advantageously include the determination of a positive and/or negative trend in a feature of a finding or an evaluation. Observation of a trend allows a link to be determined between image processing steps and their impact on result quality. Such a link can for example be used as a basis for determining optimum parameterization during image processing or a particularly favorable ratio of result quality to system resource requirement.

In an advantageous embodiment of the invention the original image data is included in the statistical analysis in addition to the processed image data. This in particular allows a quality comparison of the result of image processing with the full extent of the original image information obtained. If a feature of the processed image data is analyzed, such as the memory requirement, image processing quality can be controlled in each instance in respect of this feature by means of a comparison with the original image data.

In a further advantageous embodiment of the invention the statistical analysis takes place as a function of a result of the findings evaluation and analysis of the original image data. This means that if the result of a findings evaluation or analyses of the processed image data is also included in the analysis, the quality of the image processing steps can be controlled in respect of the result of the findings evaluation to be achieved or a diagnosis to be made. Thus for example in the medical environment a comparison can be made between the diagnosis based on the original image data with its full information content and the diagnosis based on processed image data and it can be determined which processing procedures and in some instances parameterizations during said processing procedures are sufficiently sensitive and specific in respect of a specific diagnostic question to be medically acceptable.

In a further advantageous embodiment of the invention the stored processing steps and/or in some instances processing step parameter values are also analyzed statistically. This analysis can be carried out in respect of the effectiveness of a findings evaluation or analysis, by establishing in respect of the result quality for example which processing procedures produce a result of predefined quality quickest or with the smallest outlay. The effectiveness of the findings evaluation or analysis is of major importance in everyday medical routine operation, as such work must be carried out subject to massive time and cost pressures.

BRIEF DESCRIPTION OF THE DRAWINGS

Exemplary embodiments of the invention are described in more detail below with reference to a flow diagram and a figure, in which:

FIG. 1 shows a flow diagram of the method

FIG. 2 shows a schematic illustration of a work environment.

DETAILED DESCRIPTION OF INVENTION

FIG. 1 shows a flow diagram, which illustrates the method for analyzing image processing procedures in a schematic fashion. In the first step S1 the original image data is stored. In the medical environment said original data is typically obtained by means of an imaging method, e.g. using X-ray equipment, CT or MR, and is stored either locally or in a network. Original image data is typically stored in a network in a storage and communication system (PACS=Picture Archival and Communication System) provided for this purpose.

In the next step S2 the stored original image data is retrieved for image processing and displayed for example on a screen of an image processing station. The image processing station can be either a computer connected locally to the modality and the memory unit or a findings evaluation workstation computer integrated independently of the modality in a medical network.

In the next step S3 the image data is processed. Possible processing steps can for example include compression, gray and color value modification, contrast enhancement or reduction, the highlighting of image features, the definition of contours, image focusing, noise suppression, etc. The processing steps can either be started manually and in some instances can also be parameterized manually but entire image processing procedures can also be started from a plurality of individual processing steps or image processing steps can be implemented automatically.

In the next step S4 the implemented processing steps are stored. In some instances parameter values applied in the processing steps are stored, e.g. selection of the compression algorithm, degree of compression, degree of contrast change, color scale change, etc. Depending on the result obtained, further image processing steps S3 and further storage processes S4 can follow such processing steps. The processing steps S3 and in some instances parameter values are stored such that they can be assigned to the respectively generated processed image data. In other words they are stored such that it is possible to identify subsequently which processed image data was generated by which steps. This makes is possible to assign the processing steps S3 and parameter values logically to the respective version of the processed image data, so that result quality can subsequently be associated with the steps.

In the next step S5 the processed image data is stored. It is stored either locally at the image processing workstation or in some instances centrally in the PACS. Storage takes place as described above for work steps S3 and parameter values such that mutual logical assignment is possible.

In the next step S6 statistical analysis of the image data takes place for quality control purposes. Features such as memory requirement, an image contrast measure, the number of image points selected subject to predefined criteria such as maximum brightness values, maximum contrast values, etc., can thereby be analyzed.

In the next step S7 the result of the statistical analysis is stored. It can either be stored locally or in a network environment in the PACS or on a specific quality management workstation. The result S7 is stored such that logical assignment to the analyzed stored processed image data is possible. This also allows logical assignment to the previous processing steps S3 and parameter values at the same time. In this fashion it is possible to associate the analysis result with versions of the processed image data and the processing algorithms.

In a further step S8 findings are evaluated or an analysis or diagnosis is made based on the processed image data. This can either be done by technical personnel provided for this purpose, doctors in the medical environment for example, or automatically using algorithms provided for this purpose. For example a diagnosis algorithm (CAD) can identify significant features in examination image data of the human colon (virtual colonoscopy), such as polyps, lesions on the female breast can be identified in the context of mammography examinations or stenoses can be detected in the coronary artery system. The quality of the result of the findings evaluation is a function of the result of the previous image processing steps.

Depending on the questions posed by the respective findings evaluation or diagnosis, certain processing steps or in some instances certain processing step parameter values may be more or less appropriate in order to achieve a top quality diagnosis result. The quality of the result can suffer in particular due to information loss, e.g. after image data compression. Therefore a comparison with the quality of the results of a findings evaluation based on original image data can also be carried out parallel to the findings evaluation based on the processed image data in this step S8.

In order to be able to compare result quality, in step S8 the same findings evaluation or analysis algorithms must be applied both to the original image data and to the processed image data. Such a comparison makes it possible for example to establish whether sensitivity, i.e. the probability of being able to identify an actually existing finding correctly based on the image data, has been reduced or increased by image processing or remains the same. Or it can be established whether specificity, i.e. the probability that a finding that does not actually exist will also not be established based on the image data has been increased or reduced or remains the same.

The quality of results can also be measured without knowledge of the true findings based on processed and unprocessed image data. In this instance positive ratings and negative ratings can be used, which are analyzed in an examiner-specific fashion or for a group. Additional comparisons can also be made not only between the results obtained from the original image data and the processed image data but a comparison can also be made with a known feature frequency in the examined population. If it is known for example how frequently a specific finding occurs in a specific age group, or what the trend is for the frequency of a finding for a specific gender, the image processing and findings evaluation results can be assessed in comparison with such known values.

In a final step S9 the previous image processing steps and findings evaluation steps are analyzed statistically. This makes it possible for example to establish the sequence in which specific processing steps should be carried out for maximum effectiveness or which specific processing steps produce a high quality result for a specific question with the minimum outlay. The result of the analysis can therefore include both effectiveness and result quality and it is stored as described above such that logical assignment to the respective previous processing algorithms is possible in each instance. This allows assessment of the respective algorithms in respect of the respectively analyzed quality aspect.

The described method can be deployed in the following scenario: image data is generated at a modality and transferred and stored in the unprocessed original format. It can also only be transferred partially, e.g. a specific percentage, in the original format and predefined processing algorithms can be deployed here. The transferred image data remains available as stored without modification for reference purposes. The processed image data is also stored.

The described method can be used in different system architectures—the processing algorithms can be used in a client server system for example on the client side or the server side or a combination of both.

Image processing and findings evaluation take place during routine operation, while the method described above runs automatically and in some instances without intervention by a user. Automatic analysis means that differences in findings evaluation quality or image processing quality can be detected during routine operation. The unprocessed original image data or subsets thereof can also be analyzed by experts, to be available as the gold standard and so that the processed image data can be assessed in respect of its evaluability.

Possible statistical variables relating to the results of findings evaluations or features of the processed image data, relating to individual findings images or a set of image data, and relating to the image processing step(s) applied are positive ratings (number of positive findings results), negative ratings (number of negative findings results), sensitivity, specificity, difference compared with a known feature frequency in the examined population, comparison of statistical variables before and after the application of processing steps and the effectiveness of the findings evaluation as a function of the processing procedures deployed. The effectiveness of the findings evaluation can relate to different criteria, e.g. the diagnosis reached and the correct identification of individual features and patterns.

Systematic recording of findings and findings features with assignment to the processing steps and processing step parameters applied means that it is also possible to use findings evaluator profiles to keep a statistical record of changes in result quality, which are due to the use of a specific processing step or a specific processing procedure. Thus for example a findings evaluator profile can be used to compare whether one of the said statistical variables for the result quality of said findings evaluator is influenced by a change in the processing procedure in one or a plurality of processing steps.

FIG. 2 shows a schematic illustration of a medical computer network, in which a statistical analysis of image processing procedures can be carried out. Examination data is obtained in a medical modality 20, e.g. X-ray equipment, CT or MR, or any other imaging method, and processed by an assigned modalities computer 21 to provide original data. This original image data is stored in a PACS 22 and made available for further use.

Users of the PACS 22 can retrieve the original image data from image processing workstations 24, 24', 24" for viewing or processing. An analysis or findings evaluation based on the image data is also carried out in some instances at these image processing workstations 24, 24', 24". As a result a medical diagnosis for example can be made based on the image data obtained by the modality 20.

Also connected to the medical network is a quality management workstation 25, which receives or can retrieve all the information about image processing steps, image processing step parameter values and the processed image data from the image processing workstations 24, 24', 24". The quality management workstation 25 has the task of carrying out statistical analyses on the processing procedures and the findings evaluation or analysis results. The analyzed data or analysis results are stored in a quality management memory system 26. Relevant quality information is available to the entire medical network via a quality management server 27, e.g. information in the form of recommendations in respect of image processing procedures particularly suited to specific questions or information about the sensitivity or specificity of specific findings evaluator profiles.

The network system described above is suitable for implementing the method described further above and can be used in the following exemplary instances:

EXAMPLE 1

Image data is recorded and stored in the original format. It is then processed in a predefined or interactive fashion. The processed image data is used to evaluate findings. The findings evaluation results are calculated statistically, by joint analysis of a quantity of image data processed using the same processing procedure. For example it can be established from a number of findings evaluations from mammography image data how many positive or negative findings there are and whether these ratings differ from a known frequency of positive or negative findings in the female age groups under examination.

EXAMPLE 2

Processing and analysis take place as in the example 1 outlined above, with the original image data (all or a subset thereof) also being used to evaluate findings in the same fashion. This means that either the same automatic findings evaluation algorithm is applied or that findings are evaluated based on comparable findings evaluation methods or findings evaluation criteria. Differences between the findings evaluation results for the processed images and the findings evaluation results for the original image data are then calculated, e.g. a different sensitivity for a specific findings feature or a corresponding specificity.

EXAMPLE 3

Processing and analysis take place as in the example 2 described above but the original image data is also collected in a gold standard image database, selected for example by consensus discussions or the inclusion of additional examination data.

EXAMPLE 4

The original image data has already been processed by specific processing procedures on generation and is therefore stored as already preprocessed image data and then used to evaluate findings. The findings evaluation results thus obtained are used to calculate statistical variables, which allow a conclusion to be drawn about the quality of the preprocessed image data. For example by comparing the frequency of a positive finding in a mammography examination within a specific female age group with the known frequencies of the finding for this age group it is possible to analyze the evaluability of the preprocessed image data.

EXAMPLE 5

Findings are evaluated as in the example 4 described above and a proportion of the images are stored in the unprepro-cessed original format and an analysis is carried out compared with the image data stored in its preprocessed format.

EXAMPLE 6

A multistage findings evaluation process is carried out, in which findings are evaluated during routine operation using processed image data. A selection of cases, e.g. a random selection, is used parallel to this by a quality control body to evaluate findings. Statistical analysis of the findings evaluation results during routine operation and the findings evaluation results of the quality control body, which is for example made up of specialists or particular technical experts for this purpose, can be used to verify the quality of the results during routine operation in an ongoing basis.

EXAMPLE 7

An ongoing quality check, as in example 6 described above, is carried out, with the quality control body only receiving and evaluating its findings from original image data.

EXAMPLE 8

An ongoing quality check, as in example 6 described above, is carried out, with the quality control body only receiving and evaluating its findings from the processed image data.

EXAMPLE 9

An ongoing quality check, as in example 6 described above, is carried out, with the quality control body receiving both processed image data and original image data, without however being informed which data is which. This allows a verification of statistical variables such as feature frequencies, positive ratings or negative ratings that is totally independent of individual cases to be achieved in the comparison of processed image data with original image data.

EXAMPLE 10

Ongoing quality control is carried out as in example 9 described above, with findings being evaluated from the image data during routine operation and not by the quality control body and findings evaluation results that are independent of individual cases then being obtained from processed image data in comparison with the findings evaluation from original image data.

Further exemplary embodiments can be implemented, in which the quality control body receives and evaluates all the image data for a specific case, in which the image data is distributed to more than one findings evaluator both during routine operation and in the quality control body and the results are analyzed together, in which a number of different image processing procedures are deployed, in which images processed using different image processing procedures are distributed to different groups of findings evaluators and then compared and in which findings are essentially only evaluated from images by the same findings evaluator.

The invention claimed is:
1. A method for analyzing image data, comprising:
storing unprocessed original image data in a medical computer network;
retrieving the stored image data from the medical computer network;

processing the retrieved image data by a plurality of image processing steps, each image processing step having at least one image processing parameter value related to the image processing step, each in a plurality of the image processing steps providing one of: an image enhancement including a gray or color value modification, a contrast enhancement or reduction, a highlighting of a feature in an image, contour definition, image focusing or noise suppression;

storing the image processing steps and the related image processing parameter values within the medical computer network;

evaluating the image data, processed according to the plurality of image processing steps, according to at least one statistic criterion in order to determine, among image processing steps, relative impact on image quality and optimum parameterization; and storing the processed image data together with the related image processing steps, image processing parameter values and the evaluated image data within the medical computer network.

2. The method according to claim 1, wherein the processing steps include a step chosen from the group consisting of compressing the retrieved image data, highlighting of image features included in the retrieved image data, computer-aided diagnosing the retrieved image data, processing the retrieved image data by an image data subtraction algorithm, segmenting of image areas included in the retrieved image data, suppressing noise included in the retrieved image data, enhancing an image contrast of the retrieved image data, reducing an image contrast of the retrieved image data and generating virtual image data.

3. The method according to claim 2, wherein the virtual image data represent a virtual medical endoscopy.

4. The method according to claim 1, wherein the processed image data are evaluated to form a diagnosis.

5. The method according to claim 4, wherein evaluating the processed image data according to the statistic criterion is based on the diagnosis.

6. The method according to claim 1, wherein evaluating the processed image data according to the statistic criterion is based on a characteristic of the processed image data.

7. The method according to claim 6, wherein the characteristic of the processed image data is a memory requirement of the processed image data.

8. The method according to claim 1, wherein evaluating the processed image data according to the statistic criterion is based on an element chosen from the group consisting of determining a trend with regard to a feature included in the processed image data, diagnosing the processed image data and analyzing the processed image data.

9. The method according to claim 1, wherein evaluating the processed image data according to the statistic criterion includes the original image data.

10. The method according to claim 9, wherein a diagnosis is determined based on the original image data.

11. The method according to claim 10, wherein evaluating the processed image data according to the statistic criterion is based on the diagnosis of the original image data.

12. The method according to claim 11, wherein the diagnosis according to the statistical criterion includes a comparison with a known feature frequency.

13. The method according to claim 9, wherein evaluating the processed image data according to the statistic criterion is based on a characteristic of the original image data.

14. The method according to claim 13, wherein the characteristic of the original image data includes a memory requirement of the original image data.

15. The method according to claim 1, wherein the stored image processing steps and image processing parameter values are evaluated according to a further statistical criterion.

16. The Method according to claim 15, wherein a diagnosis or evaluation effectiveness is determined based on the image processing steps and image processing parameter values evaluated according to the further statistical criterion.

17. The method according claim 1, wherein the steps of the method are executed on a client-server computer architecture.

18. The method according to claim 17, wherein the image processing steps are executed exclusively on either a server or a client of the client-server computer architecture.

19. The method according to claim 17, wherein at least one image processing step is executed on a server and a client of the client-server computer architecture such that the image processing step has a distributed software-based implementation including both the server and the client.

* * * * *